United States Patent [19]
Gittleman

[11] Patent Number: 5,885,283
[45] Date of Patent: Mar. 23, 1999

[54] OSTEOGENIC MANDIBULAR DISTENTION APPARATUS AND METHOD

[76] Inventor: Neal B. Gittleman, 99 N. Post Oak La., Apt. 420S, Houston, Tex. 77027

[21] Appl. No.: 893,657

[22] Filed: Jul. 11, 1997

Related U.S. Application Data

[63] Continuation-in-part of Ser. No. 759,790, Dec. 3, 1996, and a continuation-in-part of Ser. No. 180,237, Jan. 12, 1994, Pat. No. 5,580,247, and a continuation-in-part of Ser. No. 924,490, Aug. 4, 1992, Pat. No. 5,306,150.

[51] Int. Cl.⁶ .................................................. A61B 17/58
[52] U.S. Cl. ........................... 606/57; 606/58; 606/105; 606/69; 606/71
[58] Field of Search .................... 433/172, 173, 433/176, 215; 606/57, 58, 63, 105, 69, 70, 71

[56] References Cited

U.S. PATENT DOCUMENTS

| | | | |
|---|---|---|---|
| 5,147,358 | 9/1992 | Remmler | 606/57 |
| 5,364,396 | 11/1994 | Robinson et al. | 606/57 |
| 5,540,687 | 7/1996 | Fairley et al. | 606/57 X |
| 5,700,263 | 12/1997 | Schendel | 606/57 |
| 5,769,850 | 6/1998 | Chin | 606/105 X |

*Primary Examiner*—Nicholas D. Lucchesi
*Attorney, Agent, or Firm*—Ezra L. Schacht

[57] ABSTRACT

An apparatus and method to elongate and extend outward and downward a surgically transected forward section of the mandible with small daily adjustments to stretch the filamentary connective tissue between the divided sections of bone to correct severe malocclusion. The apparatus maintains a narrow gap between the separated sections of the mandible as the connective tissue is lengthened and mineralized forming new bone. The slowly widened gap has a chance to create new bone forming tissue to bridge the gap. By containing the apparatus within the oral cavity, advantages over cumbersome external apparatus become apparent. Infection and inflammation are easier to control within the oral environment. By clamping the apparatus to the ramus under the masseter muscles, no external facial scars result from externally applied surgical pins. Separate adjustments independently move the transected section of the mandible outward and downward.

9 Claims, 8 Drawing Sheets

OSTEOGENIC MANDIBULAR DISTENTION APPARATUS AND METHOD

This Application is a C.I.P. of application Ser. No. 08/759,790, filed on Dec. 03/1996, now pending in turn a C.I.P. of Ser. No. 08/180,237, filed Jan. 12, 1994, now U.S. Pat. No. 5,580,247, in turn a C.I.P. of Ser. No. 07/924,490, Aug. 4, 1992, now U.S. Pat. No. 5,306,150.

BACKGROUND OF THE INVENTION

To correct severe malocclusion, severe underbite or overbite, congenital micrognathia or mandibular defects from trauma or disease the applicant has devised an osteogenic mandibular distention apparatus and method that are contained within the oral cavity. An adjustable mechanism is clamped to the lateral aspect of at least one ramus under the masseter muscles and attached by surgical pins to the anterior portion of the mandible and the mandible is then transected. Daily adjustments are made to distend the anterior transected portion of the mandible while maintaining viable bone forming tissue in the transected gap.

In U.S. Pat. No. 5,540,687 Fairley et al. describes a fully sub-cutaneous device for the distraction of bones in the craniofacial region. He crafts no claims but incidentally notes: "

A further application of this device according to the invention is its use in the distraction of the mandible." Fairley et al. relies upon piercing the skin by means of a "stab incision" to reach the distraction adjustment means or "the device might include an electrical motor being activated by remote control (radio signals) in order to provide the forces required." He relies upon a single threaded spindle and mini-screw mounted plates to accomplish distraction in a single direction.

OBJECTS OF THE INVENTION

The purpose of the apparatus is to provide a means to elongate and distend the transected anterior section of the mandible with daily adjustments to stretch the filamentary connective tissue between the transected sections of bone. The apparatus maintains union as the connective tissue is lengthened and mineralized forming new bone within the transected gap. Slowly widening the gap while maintaining the integrity of the connective tissue blood supply improves the creation of new bone forming tissue. The apparatus is wholly contained within the region between the masseter muscle and the mandible and projects into the buccal vestibule. Several advantages over a cumbersome externally applied apparatus are apparent to the inventor. Infection and inflammation are easier to control within the oral environment. By clamping the apparatus to the ramus under the masseter muscles, no external facial scars result. By relying upon the ramus clamp detailed in applicant's U.S. Pat. No. 5,306,150 little or no bone surgery is required in the ramus area. The three clasps of the clamp are positioned to grasp the ramus over the sigmoid (or mandibular) notch and the posterior and anterior aspects of the ramus. The ramus clamp is rigidly secured in place by a single, easily accessible setscrew.

All parts can be fashioned from biocompatible stainless steel since this apparatus will remain in place only for the month or two while bone is formed in the lengthening gap.

DETAILED DESCRIPTION OF THE DRAWINGS

Figure 1:
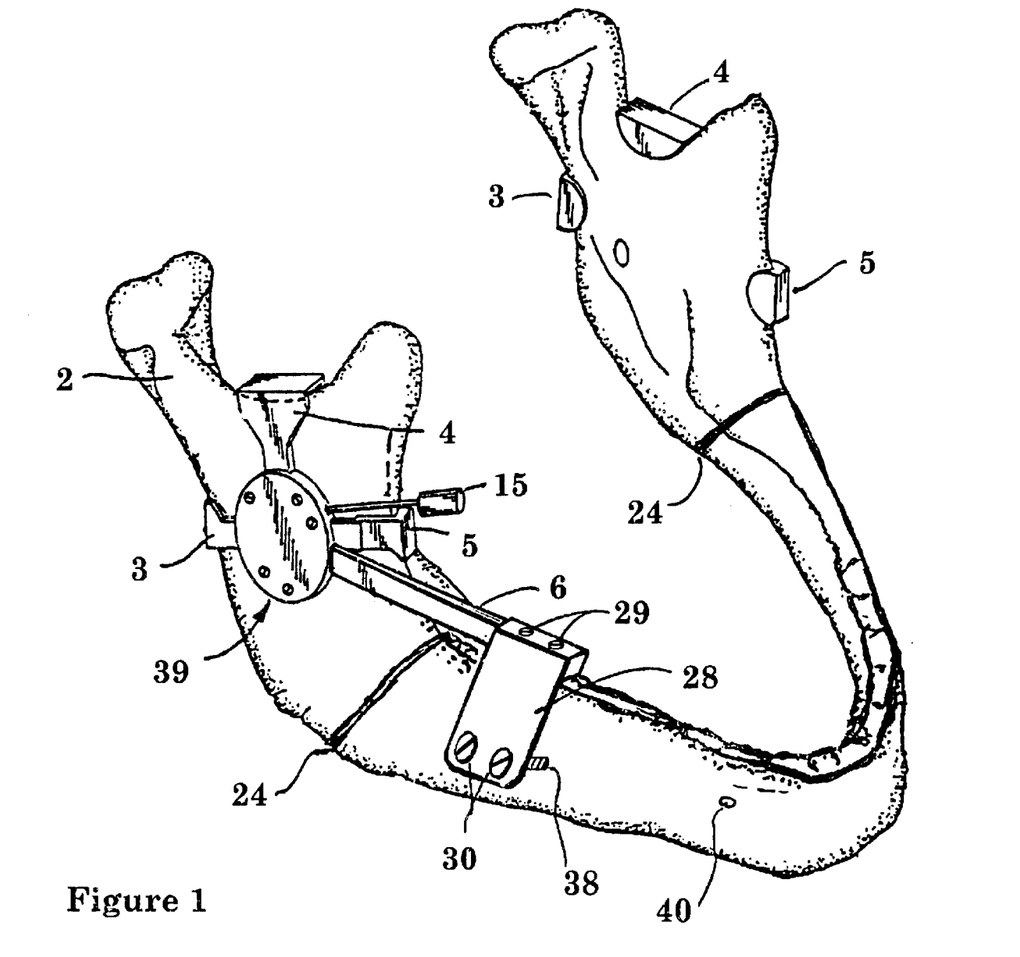
FIG. 1 shows a perspective drawing of an adjustable osteogenic distention apparatus with ramus clamping mechanism.
Figure 2:
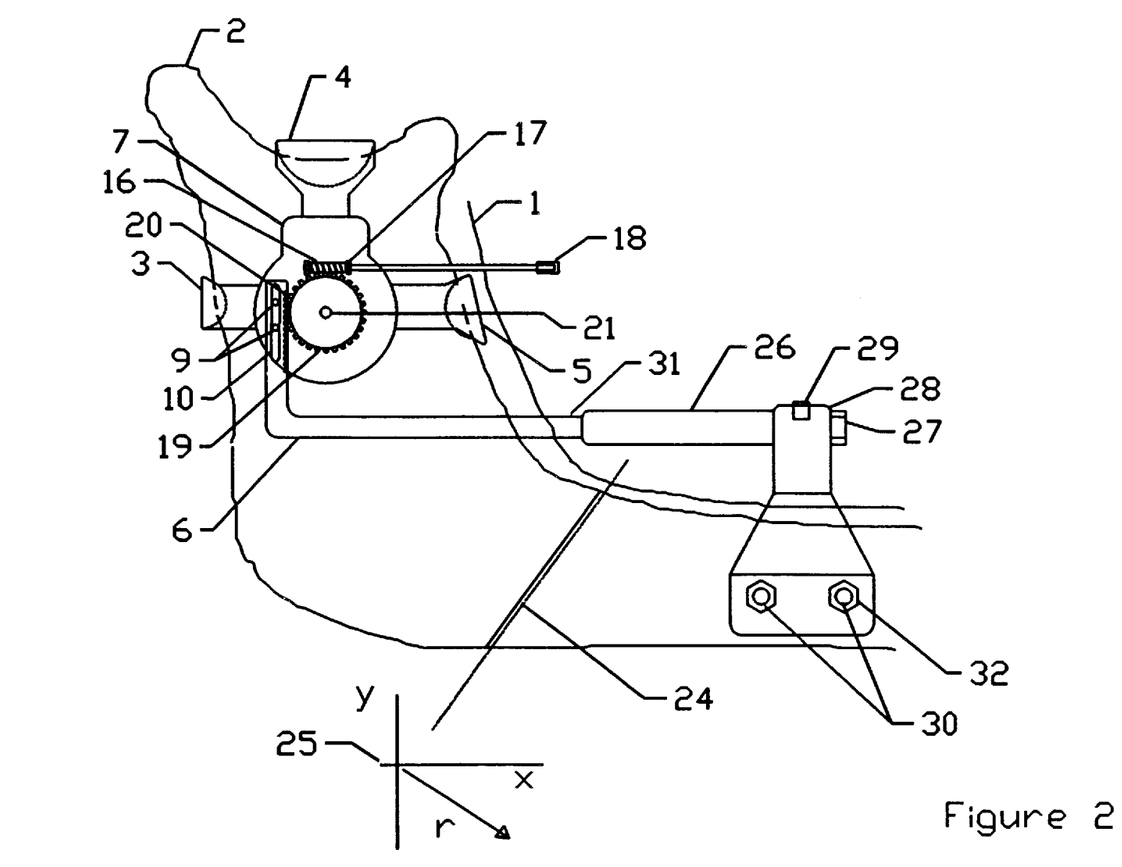
FIG. 2 shows a right lateral view of the mandible with ramus distention clamp installed. The apparatus is duplicated in mirror image for the left side of the mandible.

In a description of the embodiment of the invention, FIG. 2 shows the baseplate 7 of the ramus distention apparatus clamped to the ramus of mandible 2 by means of clasps 3, 4 and 5 as detailed in applicant's prior U.S. Pat. Nos. 5,306,150 and 5,580,247. Two mechanisms allow the independent adjustment of the distal portion of the transected mandible to be moved incrementally outward and downward. The angle and location of the transection gap 24 are chosen to form the best final mandible position while maintaining a nearly parallel tissue growth zone during the distention process. The intended resultant direction vector "r" is shown in drawing element 25. Shaft 18 fitted to worm drive 16 rotates worm gear 19 freely about pinion shaft 21 which is fixed to baseplate 7. Worm drive 16 is supported by pillow bearings 17 fixed to baseplate 7. Worm rack 20 is coupled to worm gear 19 and translates the turning adjustment of shaft 18 into a vertical linear motion of rack arm assembly 6. The rack arm assembly 6 is confined to vertical sliding motion by guide pins 9 within slot 10. Pins 9 are fixed to base plate 7. A cover (not shown) with opening for shaft 18 and rack arm 6 protects the internal mechanisms from tissue ingrowth.

The rack arm assembly 6 exits the buccal mucosa 1 and is attached by threaded stabilizing surgical pins 30 to the lateral aspect of the mandible. Horizontal distention means 26 adjusts the length of rack arm assembly 6. Bracket 28 with locking means 29 rigidly holds stabilizing surgical pins 30 in alignment with rack arm 6. Hex-ended shaft 27 drives the horizontal distention means 26 resulting in daily incremental horizontal motion with the increased new bone-forming tissue growth in the widening transected gap in the mandible. The gap is widened approximately 1 mm per day until the final position of the anterior portion of the mandible is obtained. A partial or full turn of shaft 18 results in an equivalent downward motion of the anterior portion of the transected mandible each day.

Figure 3A:
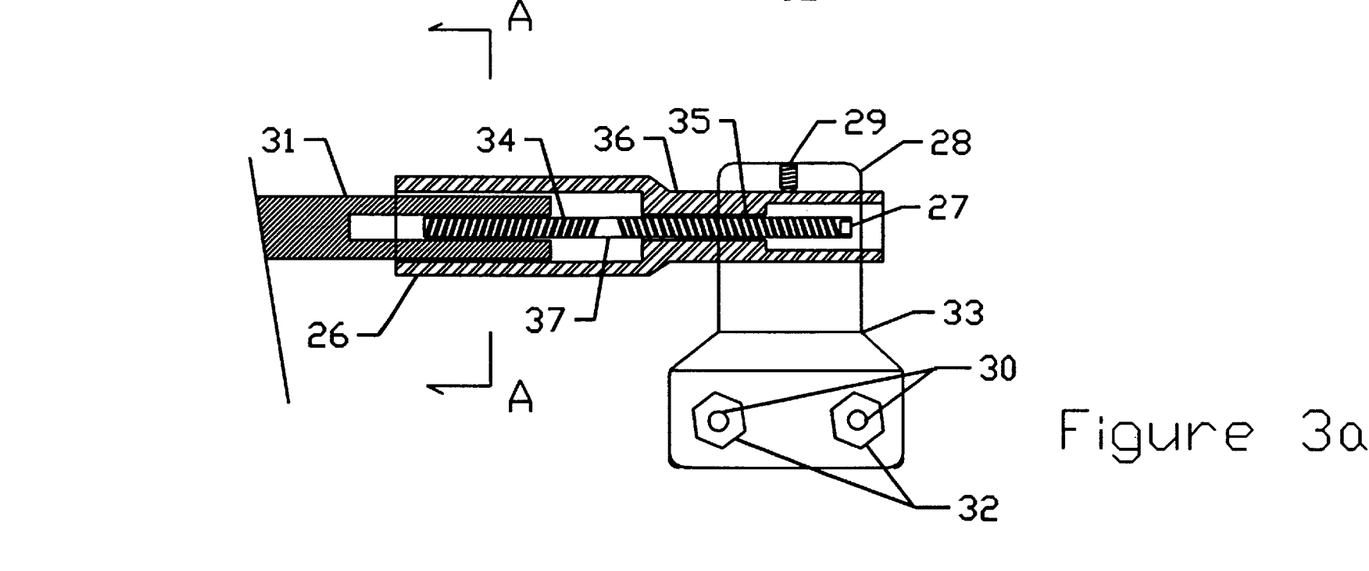
FIG. 3a shows a detailed view of the horizontal distention means.

The horizontal distention means detailed in FIG. 3a consists of an adjustable extension 26 connected to arm 31 by means of rotating shaft 37 having a right-handed threaded section 34 and a left-handed threaded section 35. Shaft 37 when rotated by means of hex-ended wrench (not shown) inserted within hexed hollow 27 moves extension 26 along the arm 31. The rectangular cross-section of arm 31 within mating rectangular hollow guideway of adjustable extension 26 prevents rotation of extension 26 about arm 31 as detailed in FIG. 3*b*. By using machined threads of opposite handedness on shaft 37 and mating machine threads matching said handedness within the end of arm 31 and extension 26, bracket 29 is moved inward with the clockwise turning of shaft 37 and outward with the counter-clockwise turning of shaft 37. The amount of outward horizontal extension per turn of shaft 37 can be controlled by using different thread pitches having more threads per unit length in the threaded portions 34 than in threaded portion 35 of shaft 37. Mating threads in arm 31 and portion 36 of extension 26 match those of shaft 37 threads 34 and 35 respectively.

Bracket 28 is fixed to extension 26 by at least one set screw 29 at the appropriate angle on the extension 26 to mate the bracket to threaded surgical pins 30 set into the anterior transected section of the mandible. Suitable means 32 secure and lock in place threaded surgical pins to bracket 28. A hexagonal captive nut 32 freely rotates in a round hole in bracket 28. The captive nuts engage the threads of pins 38. As detailed in the end view, FIG. 3*c*, bracket 28 is has an offset relief bend at 33 to accommodate the outward curvature of the lateral aspect of the mandible and to position the threaded surgical pins 38 to enter the lateral aspect of the anterior portion of the mandible at a safe and secure angle.

Figure 4:
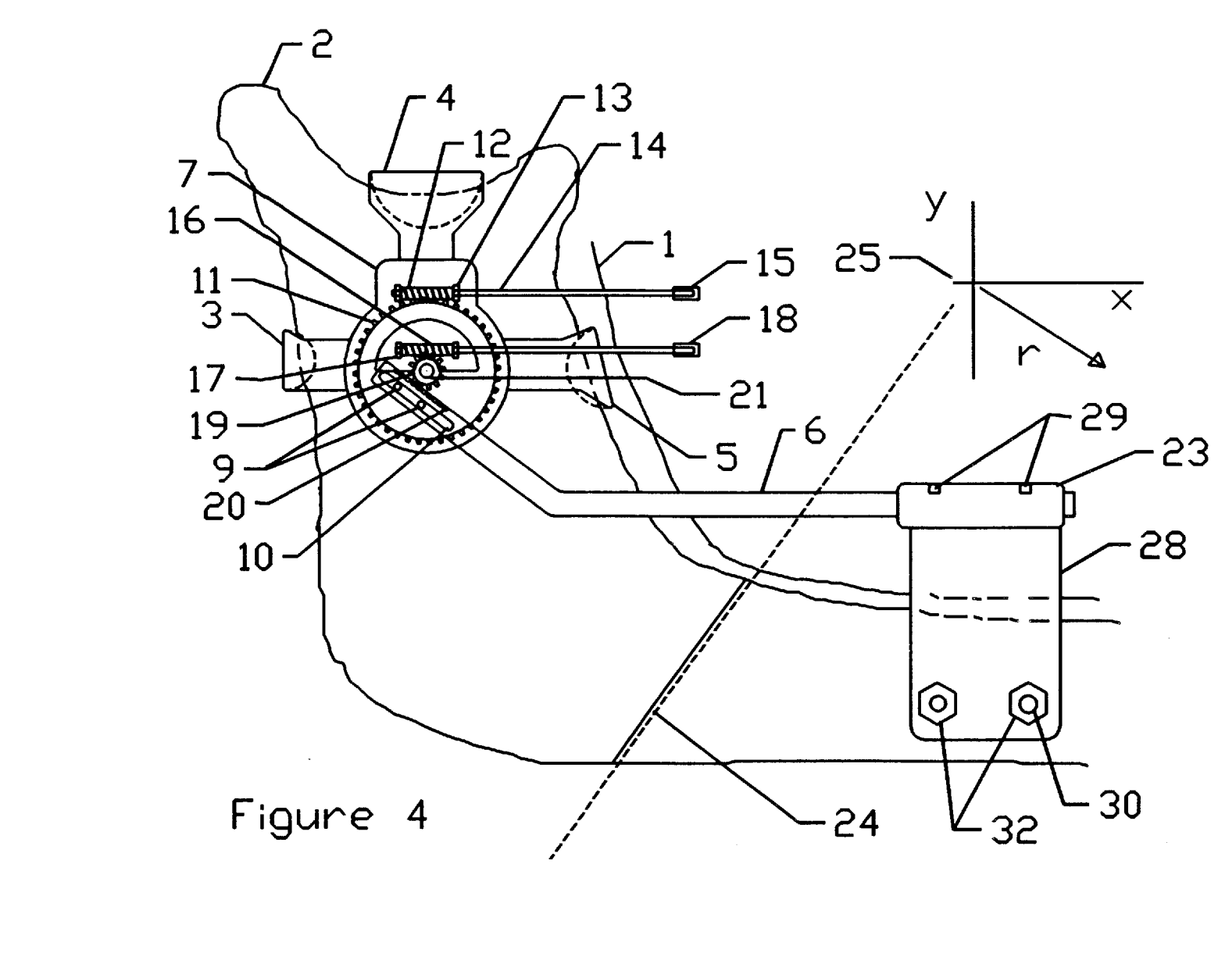
FIG. 4 details a lateral view of an alternate apparatus to adjust angular and linear motion of the transected portion of the mandible.

The embodiment of the invention detailed in FIG. 4 describes an alternate dual adjustment mechanism, altering both angular and horizontal motion in two adjustments made to gradually move the transected anterior portion of the mandible forward and downward.

The rotary motion is accomplished by turning flexible shaft 14 fixed to worm drive 12. Worm drive 12 rotates toothed worm gear 11 around fixed support shaft 21 set in base plate 7. The free end of arm 6 which is attached by surgical pins 30 to the anterior portion of the mandible is rotated downward by turning shaft 14 counter clock wise by means of hexagonal head 15. Worm drive 12 is maintained in alignment by bearing blocks 13 mounted to the baseplate 7.

The second motion to elongate the mandible consists of an outward extension of arm 6 in a direction perpendicular to the line of transection. This is accomplished by turning shaft 18 fixed to worm drive 16 which rotates toothed worm gear 19 independently about shaft 21. Worm rack 20 moves arm 6 outward as constrained by pins 9 in slot 10. Pins 9 are secured to the face of gear 11. Gear 19 rotates independently from gear 11 about the same shaft 21. A clockwise turning of shaft 18 results in the outward extension of the transected anterior portion of the mandible which is attached to the distant end of arm 6. Gear 11 is shown with a relief window for worm drive 16 and its bearing blocks 17. The bearing blocks 17 are attached to baseplate 7 and support and align shaft 18 and worm drive 16.

A cover cap (not shown) protects the gear mechanisms from the binding invasion of tissue. Bracket 23 fixed to arm 6 by set screws 29 hold the anterior transected portion of the mandible by rigid connection to surgical pins 30. The combined adjustments of shafts 14 and 18 allow the practitioner to arrive at a near perfect final alignment. Shafts 14 and 18 can be made of flexible members and terminated at the free end with an external hex head that can easily be rotated by a socket-end wrench where they protrude through the oral mucosa. The flexible shafts can be fashioned with an external hexagonal cross section to allow the surgeon to clip them to a comfortable length and still attach a socket-end wrench for manipulation.

Figure 5:
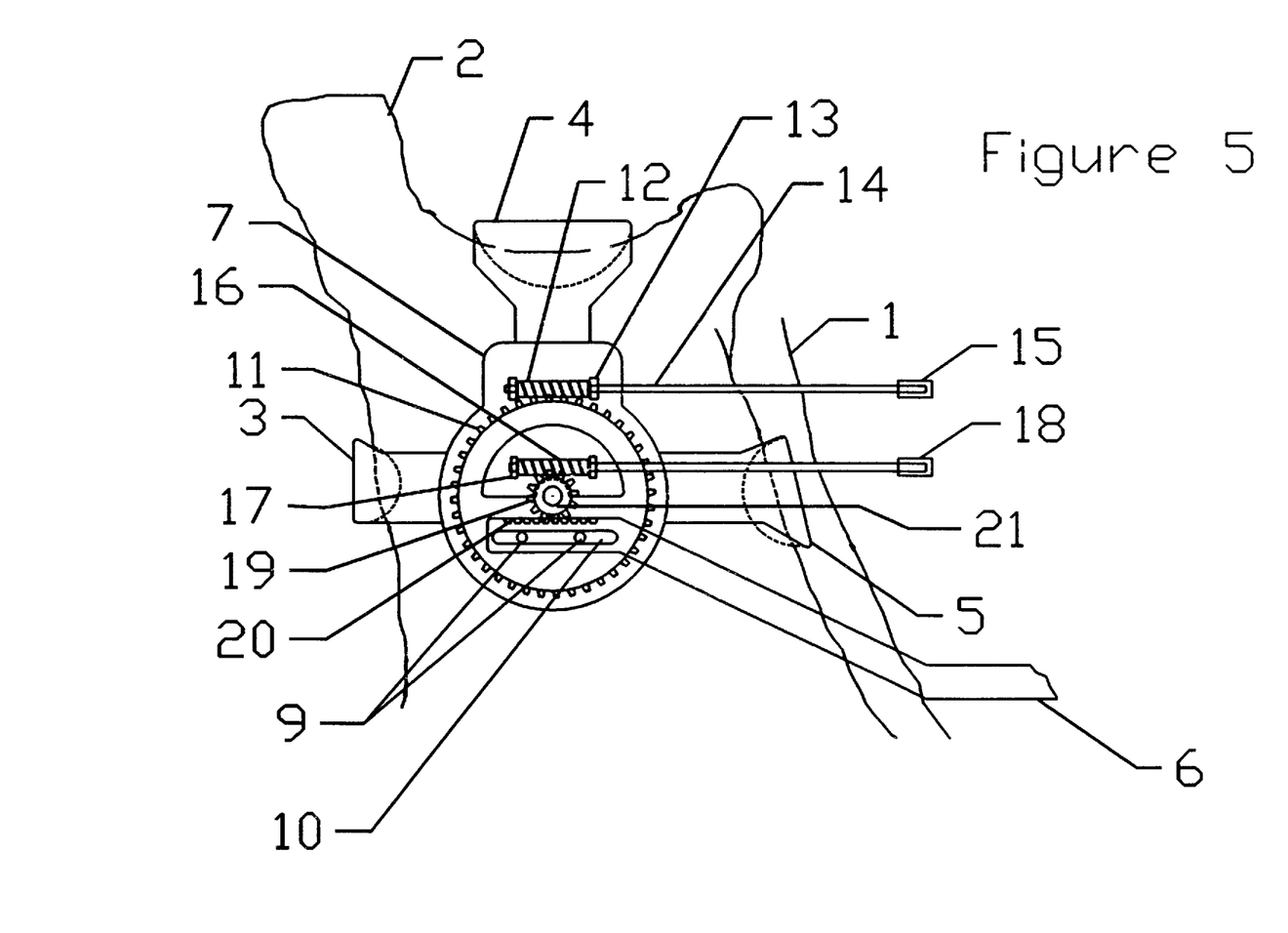
FIG. 5 shows a lateral view of an alternate apparatus to adjust angular and linear motion independently.

The invention, in an alternate embodiment in FIG. 5, shows the baseplate 7 of the apparatus is rigidly held by means of clasps 3, 4 and 5 to secure the baseplate to the lateral aspect of ramus as divulged in prior U.S. Pat. Nos. 5,306,150 and 5,580,247. The clamping mechanism is hidden from view under baseplate 7 is formed from stainless steel or other suitably strong, biocompatible material.

A dual adjustment mechanism, altering both angular and horizontal motion in two adjustments made to gradually move the transected anterior portion of the mandible forward and downward. The rotary motion is accomplished by turning flexible shaft 14 fixed to worm drive 12. Worm drive 12 rotates toothed worm gear 11 around fixed support shaft 21 set in base plate 7. The free end of arm 6 which is attached by surgical pins to the anterior portion of the mandible (not shown) is rotated downward by turning shaft 14 counter clock wise by means of hexagonal head 15. Worm drive 12 is maintained in alignment by bearing blocks 13 mounted to the baseplate 7.

The second motion to elongate the mandible consists of an horizontal outward extension of arm 6. This is accomplished by turning shaft 18 fixed to worm drive 16 which rotates toothed worm gear 19 independently about shaft 21. Worm rack 20 moves arm 6 outward as constrained by pins 9 in slot 10. Pins 9 are secured to the face of gear 11. Gear 19 rotates independently from gear 11 about the same shaft 21. A clockwise turning of shaft 18 results in the outward extension of the transected anterior portion of the mandible which is attached to the distant end of arm 6(not shown). Gear 11 is shown with a relief window for worm drive 16 and its bearing blocks 17. The bearing blocks 17 are attached to baseplate 7 and support and align shaft 18 and worm drive 16. A cover cap (not shown) protects the gear mechanisms from the binding invasion of tissue. A bracket is fixed to arm 6 holds the anterior transected portion of the mandible by rigid connection to surgical pins. The combined adjustments of shafts 14 and 18 allow the practitioner to arrive at a near perfect final alignment. Shafts 14 and 18 can be made of flexible members and terminated at the free end with an external hex head that can easily be rotated by a socket-end wrench where they protrude through the oral mucosa. The flexible shafts can be fashioned with an external hexagonal cross section to allow the surgeon to clip them to a comfortable length and still attach a socket-end wrench for manipulation.

Figure 3B:
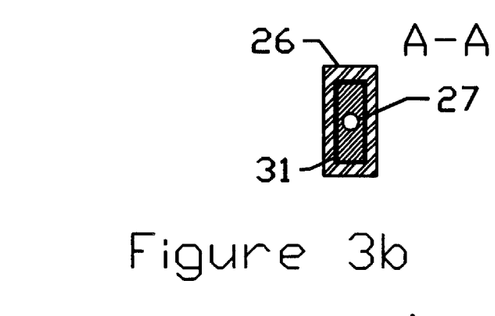
FIG. 3b is a sectional view of the distention apparatus.
Figure 3C:
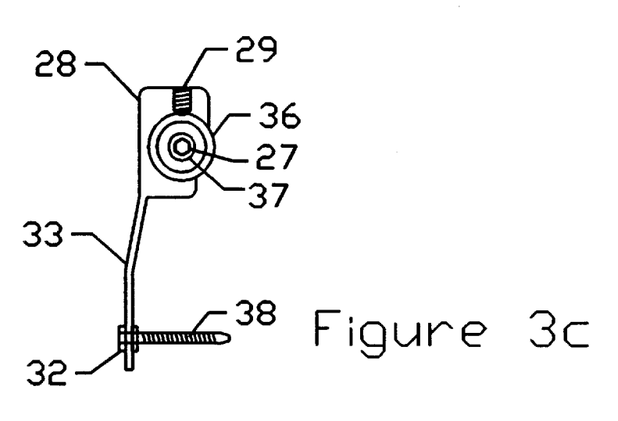
FIG. 3c is a distal end view of the distention bracket assembly.
Figure 6:
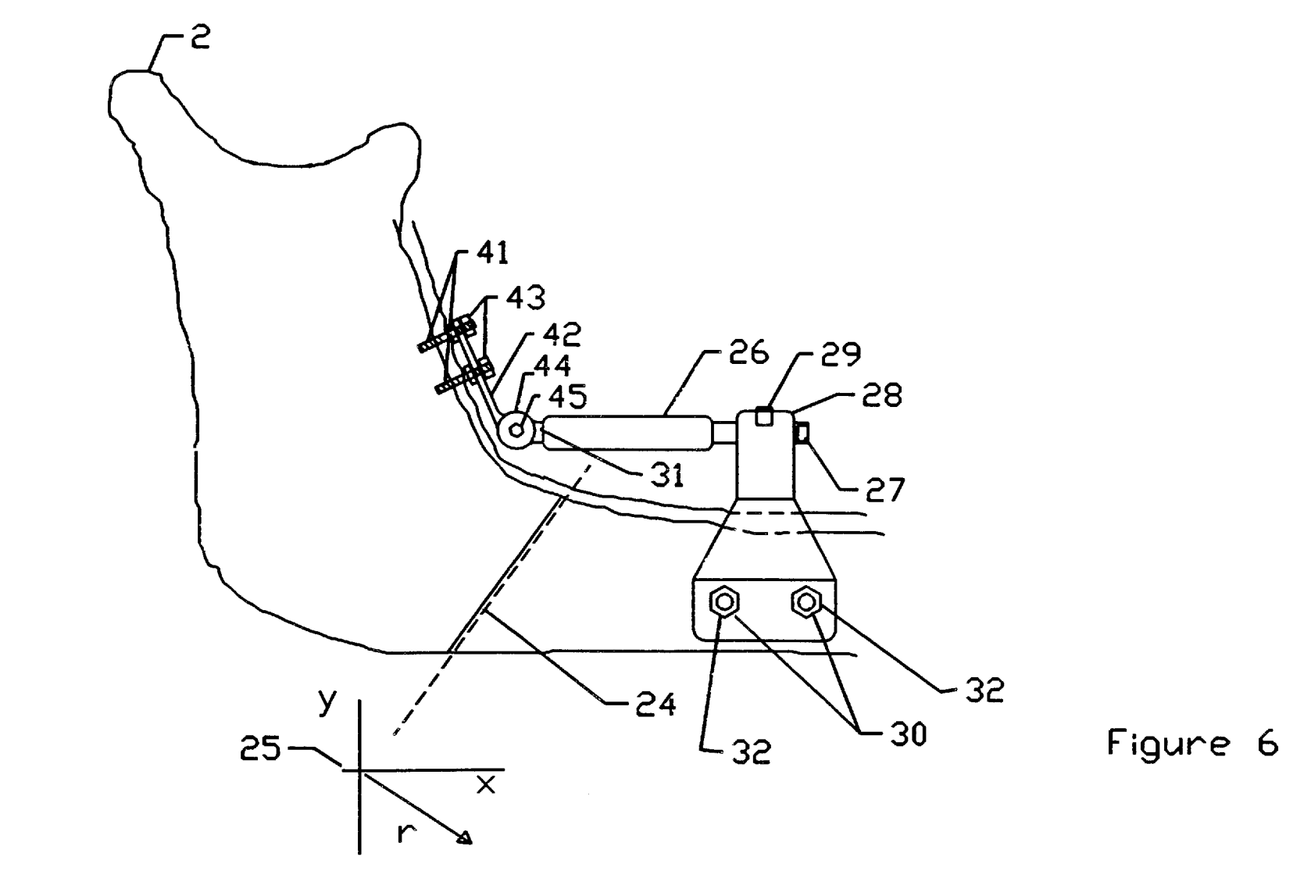
FIG. 6 is a right lateral view of an adjustable mandibular distention apparatus secured to the anterior aspec of the oblique angle portion of the ramus by surgical pins.

Another embodiment of the invention recognizes the temporary nature of the apparatus to distend the transected portion of the mandible and secures the apparatus by means of temporary collared surgical pins installed in the anterior oblique angle portion of the ramus. FIG. 6 shows pins 41 threaded into predrilled holes in the anterior oblique angle portion of the ramus 2 exiting through the mucosa 1. Pins 41 are shown with supporting collars acting as platforms for bracket 42. The pins 41 are driven into the ramus leaving enough gap between the supporting collars and the mucosa to prevent tissue damage. Mating holes in bracket 42 fit pins 41 and are fixed in place on pins 41 by means of self locking nuts 43. Angular adjustment element 44 is locked at the correct distention angle by locking means 45 thereby securing arm 31 in a rigidly fixed position on the ramus. Details in FIGS. 3*a*, 3*b* and 3*c* show the horizontal distention means consisting of an adjustable extension 26 connected to arm 31 by means of rotating shaft 37 having a right-handed threaded section 34 and a left-handed threaded section 35. Shaft 37 when rotated by means of hex-ended wrench (not shown) inserted within hexed hollow 27 moves extension 26 along the arm 31. The rectangular cross-section of arm 31 within mating rectangular hollow guideway of adjustable extension 26 prevents rotation of extension 26 about arm 31 as detailed in FIG. 3b. By using machined threads of opposite handedness on shaft 37 and mating machine threads matching said handedness within the end of arm 31 and extension 26, bracket 29 is moved inward with the clockwise turning of shaft 37 and outward with the counter-clockwise turning of shaft 37. Bracket 28 is fixed to extension 26 by at least one set screw 29 at the appropriate angle on the extension 26 to mate the bracket to threaded surgical pins 30 set into the transected section of the mandible. Suitable means 32 secure and lock in place threaded surgical pins to bracket 28. A hexagonal captive nut 32 freely rotates in a round hole in bracket 28. The captive nuts engage the threads of pins 38. As detailed in the end view, FIG. 3c, bracket 28 is has an offset relief bend at 33 to accommodate the outward curvature of the lateral aspect of the mandible and to position the threaded surgical pins 38 to enter the lateral aspect of the anterior portion of the mandible at a safe and secure angle. Surgical pins 38 can be equipped with collars to prevent bracket 33 from bearing directly against the mucosa.

Angular adjustment element 44 and locking means 45 can be replaced by a vertical compound-threaded, linear distention mechanism.

Figure 7A:
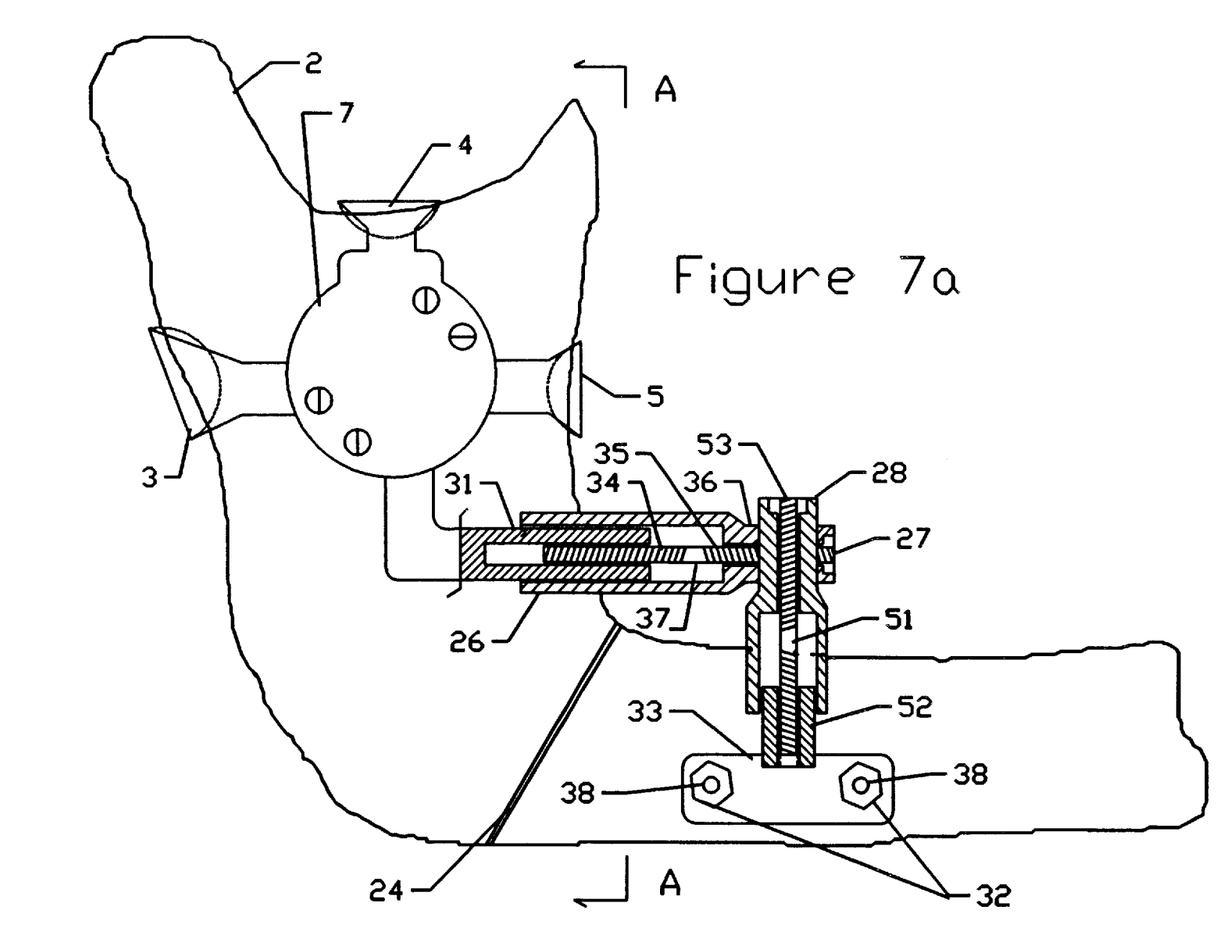
FIG. 7a details a lateral view of a distention apparatus with independent horizontal and vertical compound screw distention adjustments connected to a ramus clamp apparatus.
Figure 7B:
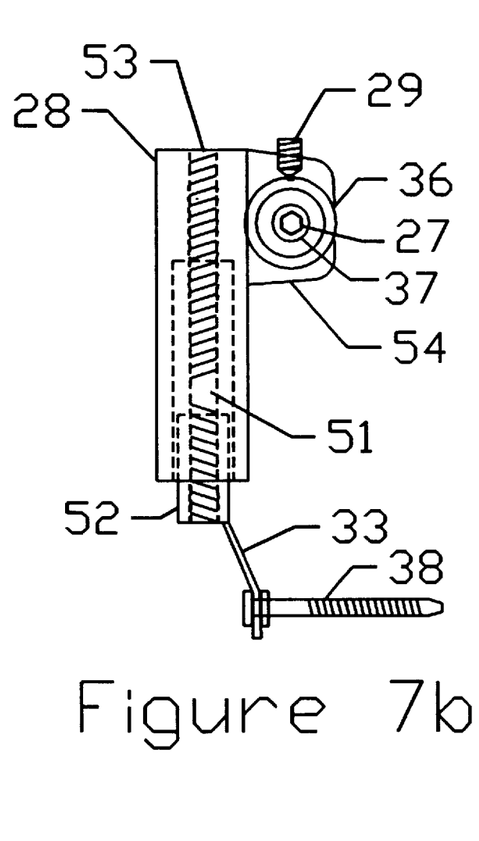
FIG. 7b is a distal end view of a distention apparatus with independent horizontal and vertical compound screw distention adjustments.

A pair of compound-threaded, linear distention mechanisms clamped together at right angles offer another method of making independently discrete periodic horizontal and vertical manipulations to the transected anterior portion of the mandible. FIG. 7a and 7b show this embodiment of the distention apparatus in which the adjustments to the transected portion of the anterior mandible are secured by means of surgical pins 38 to contoured bracket 33. The bracket assembly 33 is moved vertically by means of compound threaded screw shaft 53. Screw shaft 53 has a left-handed threaded portion and a right-handed threaded portion engaging a left-handed threaded cylindrical opening in housing 28 and a right-handed threaded cylindrical opening in sliding element 52. Sliding element 52 has a rectangular cross section that prevents it turning within housing 28. Screw shaft 53 can be turned by means of a suitable tool, such as an Allen wrench, to elevate or lower the anterior transected portion of the mandible.

As detailed in FIG. 7b, vertical housing 28 is clamped to horizontal housing 26 by means of surrounding grip 54 with at least one set screw 29. The grip can be radially positioned about housing 26 before tightening with set screw 29 to allow for the outward angle of the mandible.

Figure 7C:
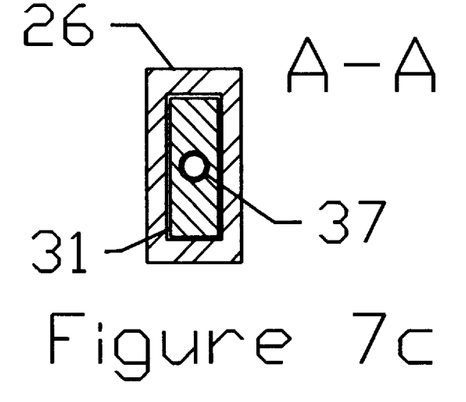
FIG. 7c is a cross section through a portion of a distention apparatus.

Horizontal housing 26 is moved along arm 31 by the same type of compound screw mechanism used in the vertical distention element. By turning compound shaft 37 having left-handed and right-handed threaded portions by means of a suitable tool at shaft end 27, the housing 26 is moved inward or outward along arm 31. The rectangular cross section of arm 31, as detailed in FIG. 7c, prevents housing 26 from rotating around arm 31. Arm 31 is rigidly attached to a ramus 2 by clasps 3, 4 and 5. By alternately adjusting compound shafts 37 and 51 transection gap 24 can be lengthened and lowered in any proportion.

What is claimed is:

1. A clamp securable non-invasively to at least one ramus portion of the mandible of a patient, the clamp having clasping means for engaging with curved surfaces of said at least one ramus portion, said clamp supporting an arm adapted attached to a surgically transected anterior portion of said mandible, said clamp adapted to be contained sub-dermally between the masseter muscle and at least one lateral aspect of the ramus of said mandible, said arm having means to firmly hold said anterior transected portion of said mandible, said arm having independent horizontal extension means to distend horizontally, and having independent vertical extension means to distend vertically said anterior transected portion of said mandible;

said independent horizontal extension means and said independent vertical extension means respectively having independent horizontal adjustment means and independent vertical adjustment means adapted to be accessible within the buccal cavity of a patient by an adjustment tool;

while osteogenesis occurs over time in a periodically adjusted distention gap in said mandible.

2. A clamp as recited in claim 1, where said arm is fixed to said clamp;

said arm protruding transmucosally into said buccal cavity of said clamp; and wherein said independent horizontal extension means and said independent vertical extension means and said independent horizontal adjustment means and said independent vertical adjustment means connected to said arm are adapted to be wholly contained within the buccal cavity of said patient.

3. A clamp as recited in claim 1, where said horizontal extension means and said vertical extension means are integral with said clamp and are adapted to be located between the masseter muscle and said at least one ramus of the mandible;

said arm being movable by said horizontal extension means and said vertical extension means;

said arm adapted to protrude transmucosally into the buccal cavity of said patient;

the independent adjustment means of said horizontal extension means and the independent adjustment means of said vertical extension means adapted to protrude transmucosally and flexibly within said buccal cavity of said patient;

wherein a mating tool is periodically and independently engaged with said horizontal adjustment means and said vertical adjustment means to distend said transected gap in said mandible.

4. A clamp securable non-invasively to at least one ramus portion of the mandible of a patient, the clamp having clasping means for engaging with curved surfaces of said at least one ramus portion, said clamp supporting an arm adapted to be attached to a surgically transected anterior portion of the mandible, said clamp adapted to be contained sub-dermally between the masseter muscle and the lateral aspect of the at least one ramus of said mandible, said arm having means to firmly hold said transected anterior portion of said mandible, said arm having independent horizontal extension means to distend horizontally and independent radial extension means to distend radially said transected anterior portion of the mandible;

said independent horizontal extension means and said independent radial extension means respectively having independent horizontal adjustment means and independent radial adjustment means adapted to be accessible within the buccal cavity of said patient by an adjustment tool.

5. A clamp securable non-invasively to at least one ramus portion of the mandible of a patient, the clamp having clasping means for engaging with curved surfaces of said at least one ramus portion, said clamp supporting an arm attached to a surgically transected anterior portion of the mandible, said clamp adatped to be contained sub-dermally between the masseter muscle and the lateral aspect of the at least one ramus of said mandible, said arm having means to firmly hold said transected anterior portion of said mandible, said arm having independent vertical extension means to distend vertically and independent radial extension means to distend radially said transected anterior portion of the mandible;

said independent vertical extension means and said independent radial extension means respectively having independent vertical adjustment means and independent radial adjustment means adapted to be accessible within the buccal cavity of said patient by an adjustment tool.

6. A clamp securable non-invasively to at least one ramus portion of the mandible of a patient, the clamp having clasping means for engaging with curved surfaces of said at least one ramus portion, said clamp supporting an arm adapted to be attached to a surgically transected anterior portion of the mandible, said clamp adapted to be contained sub-dermally within the sub-masseter region of said mandible, said arm having means to firmly hold said anterior portion of the mandible, said arm having independent horizontal extension means to distend vertically and independent radial extension means to distend radially said anterior portion of the mandible;

said independent vertical extension means and said independent radial extension means respectively having independent vertical adjustment means and independent radial adjustment means adapted to be accessible by an adjustment tool within the buccal cavity of said patient;

the independent adjustment means of said vertical extension means and the independent adjustment means of said radial extension means adpated to extend transmucosally and flexibly to within said buccal cavity wherein a mating tool is periodically and independently engaged with said vertical adjustment means and said radial adjustment means to distend a transected gap in said mandible.

7. A method of installing a non-invasive clamp securable to the ramus portion of a mandible of a patient, said clamp comprising a superior securing clasp, an anterior securing clasp and a posterior securing clasp, and an extensible arm with adjustable distention means with a distal end securably mountable to the anterior aspect of said mandible, said method comprising:
(a) exposing said ramus portion by incising through the mucosa in the area of the external oblique ridge;
(b) exposing the ascending portion of said ramus portion from the retromolar region superiorly to the coronoid tip;
(c) dissecting posteriorly to expose the sigmoid notch of said ramus portion and uncovering the lateral aspect of the ramus portion while exposing the angle of said mandible and its inferior border;
(d) placing both said superior and said posterior securing clasps onto said sigmoid notch and posterior border respectively;
(e) seating said clamp into position and locking said clamp in place;
(f) securably mounting the distal end of said adjustable distention arm to the anterior aspect of the mandible wholly within the buccal cavity of the patient,
(g) transecting the mandible,
(h) suturing said mucosa about a portion of said adjustable distention arm protruding into said buccal cavity, and
(i) periodically adjusting said adjustable distention means to extend said anterior portion of the mandible while osteogenesis occurs in the transected gap of the mandible.

8. A bracket securable rigidly by fastening means to at least one ramus portion of the mandible of a patient, the bracket supporting an arm adapted to be attached to a surgically transected anterior portion of said mandible, said bracket adapted to be contained sub-dermally between the masseter muscle and the lateral aspect of said at least one ramus portion of said mandible, said arm having means to firmly hold said anterior transected portion of said mandible, said arm having independent lengthwise extension means, and said arm having independent angular extension means to distend said anterior transected portion of said mandible;

said independent lengthwise extension means and said independent angular extension means respectively having independent adjustment means adapted to be accessible within the buccal cavity of said patient by an adjustment tool;

while osteogenesis occurs over time in a periodically adjusted distention gap in said mandible.

9. A bracket as recited in claim 8 in which said independent angular extention means is a adapted to be replaced with an independently adjustable vertical extention means.

* * * * *